US010053442B2

(12) United States Patent
De Sousa Dias et al.

(10) Patent No.: US 10,053,442 B2
(45) Date of Patent: *Aug. 21, 2018

(54) PREPARATION OF DIALKYL ESTERS OF 2,5-FURANDICARBOXYLIC ACID

(71) Applicant: Synvina C.V., Amsterdam (NL)

(72) Inventors: Ana Sofia Vagueiro De Sousa Dias, Amsterdam (NL); Benjamin McKay, Amsterdam (NL); Victor Peter Charles Vreeken, Amsterdam (NL); Johannes Maria Franciscus Sijben, Amsterdam (NL)

(73) Assignee: Synvina C.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/525,424

(22) PCT Filed: Nov. 10, 2015

(86) PCT No.: PCT/NL2015/050780
§ 371 (c)(1),
(2) Date: May 9, 2017

(87) PCT Pub. No.: WO2016/076710
PCT Pub. Date: May 19, 2016

(65) Prior Publication Data
US 2017/0313670 A1   Nov. 2, 2017

(30) Foreign Application Priority Data
Nov. 10, 2014   (NL) ...................................... 2013764

(51) Int. Cl.
C07D 307/02   (2006.01)
C07D 307/68   (2006.01)

(52) U.S. Cl.
CPC ................................ *C07D 307/68* (2013.01)

(58) Field of Classification Search
CPC ....................................................... C07D 307/68
USPC .......................................................... 549/485
See application file for complete search history.

(56) References Cited

U.S. PATENT DOCUMENTS

| 8,519,167 B2 | 8/2013 | Munoz De Diego et al. |
| 2012/0220507 A1 | 8/2012 | Grass et al. |
| 2012/0302768 A1 | 11/2012 | Janka et al. |

(Continued)

FOREIGN PATENT DOCUMENTS

| WO | 2011/043661 A1 | 4/2011 |
| WO | 2013/191938 A1 | 12/2013 |

*Primary Examiner* — Taylor V Oh
(74) *Attorney, Agent, or Firm* — Hoffmann & Baron, LLP

(57) ABSTRACT

Dialkyl esters of 2,5-furandicarboxylic acid are prepared from a 2,5-furandicarboxylic acid-containing starting material in a process, which includes: contacting a vaporous stream of an alkanol countercurrently with the at least partially liquid starting material having the 2,5-furandicarboxylic acid, in a reaction zone to conduct an esterification reaction to yield the dialkyl ester of 2,5-furandicarboxylic acid and water; withdrawing a reaction vapor comprising the alkanol and water from the reaction zone; and discharging a liquid phase having at least the dialkyl ester of 2,5-furandicarboxylic acid, from the bottom part of the reaction zone, to obtain the dialkyl ester of 2,5-furandicarboxylic acid.

20 Claims, 1 Drawing Sheet

(56) References Cited

U.S. PATENT DOCUMENTS

2013/0345449 A1* 12/2013 Partin .................. C07D 307/68
549/485

* cited by examiner

PREPARATION OF DIALKYL ESTERS OF 2,5-FURANDICARBOXYLIC ACID

CROSS-REFERENCE TO RELATED APPLICATIONS

This application is the National Stage of International Application No. PCT/NL2015/050780 filed Nov. 10, 2015, which claims the benefit of Netherlands Application No. NL 2013764, filed Nov. 10, 2014.

FIELD OF THE INVENTION

The present invention relates to a process for the preparation of dialkyl esters of 2,5-furandicarboxylic acid. More in particular it relates to the preparation of such esters by means of a countercurrent contact between a vaporous alkanol and 2,5-furandicarboxylic acid in a liquid phase.

BACKGROUND OF THE INVENTION 2,5-Furandicarboxylic acid ("FDCA") is a dicarboxylic acid for which the commercial interest has grown recently. The diacid or its diester has been found to be particularly interesting for the preparation of poly(alkylene-2,5-furandicarboxylate), in which preparation FDCA is condensed with an alkylene glycol, such as monoethylene glycol (MEG). The polymer obtained from the polymerization of FDCA or its diester and MEG, polyethylene-2,5-furandicarboxylate (PEF), can be used as alternative for polyethylene terephthalate (PET) or, due to its properties, can be used in areas where PET cannot be used. As one of the advantages of using FDCA it is considered that FDCA is obtainable from sustainable sources. In WO 2011/043661 and U.S. Pat. No. 8,519,167 methods are described wherein 5-hydroxymethyl furfural and derivatives thereof are converted into FDCA and esters thereof. As explained in these patent documents, the starting material 5-hydroxymethylfurfural and derivatives thereof can be obtained from carbohydrate-containing sources, such as fructose, glucose, sucrose, starch, cellulose etc.

US 2012/0302768 discloses that the oxidation process of 5-hydroxymethylfurfural and derivatives thereof leads to the formation of a mixture of 2,5-furan-dicarboxylic acid, 2-formyl-furan-5-carboxylic acid and, optionally, some other furan derivatives, such as alkyl esters of 2-formyl-furan-5-carboxylic acid. Although it is stated that purified 2,5-furandicarboxylic acid can be obtained by washing, it was found that also the purified product still contained an amount of 2-formyl-furan-5-carboxylic acid. It is acknowledged in US 2012/0302768 that significant concentrations of mono-functional molecules like 2-formyl-furan-5-carboxylic acid in the 2,5-furan-dicarboxylic acid product are particularly detrimental to polymerization processes as they may act as chain terminators during a polyester condensation reaction.

It has been found that washing does not yield pure product. It is believed that 2-formyl-furan-5-carboxylic acid is included in the crystals of 2,5-furan-dicarboxylic acid whereby the purification by washing becomes unfeasible. Purification of the corresponding ester products was found to be easier.

The need for a method for the production and purification of esterification products of FDCA has been acknowledged in WO 2013/191938. In order to meet this need WO 2013/191938 describes a process wherein a liquid reaction mixture comprising FDCA, an alcohol, water, the monoester and the diester of FDCA, is subjected to esterification. The esterification product is vaporized such that a vapor comprising the mono- and diester of FDCA, unreacted alcohol and water, is removed from the reaction mixture and passed to a rectification zone. In the rectification zone at least a portion of the monoester of FDCA is condensed and the liquid monoester is subsequently contacted with the reaction mixture. The diester of FDCA is continuously discharged for the rectification zone, together with water, unreacted alcohol and by-products.

A drawback of this process resides in that the vaporized esterification product removes not only water, but also the alcohol and the mono- and diester of FDCA. Therefore, the vapor stream is large, which requires a high amount of energy. Further, due to the range of boiling points of the components of the vapor, i.e. water, alcohol, monoester and diester of FDCA, the rectification is complicated. Moreover, by the removal of the monoester together with the alcohol and water the production of the desired diester of FDCA is sub-optimal. Hence, there is a need for a process for the preparation of alkyl esters of FDCA, wherein the separation of the various components in the reaction mixture is facilitated and the yield of the esterification reaction is improved compared to this known process.

SUMMARY OF THE INVENTION

Accordingly, the present invention provides a process for the preparation of dialkyl esters of 2,5-furandicarboxylic acid from a 2,5-furandicarboxylic acid-containing starting material, which process comprises:
  contacting a vaporous stream of an alkanol countercurrently with the at least partially liquid starting material comprising the 2,5-furandicarboxylic acid in a reaction zone to conduct an esterification reaction to the dialkyl ester of 2,5-furandicarboxylic acid and water;
  withdrawing a reaction vapor comprising the alkanol and water from the reaction zone;
  discharging a liquid phase comprising at least the dialkyl ester of 2,5-furandicarboxylic acid, from the bottom part of the reaction zone, to obtain the dialkyl ester of 2,5-furandicarboxylic acid.

By contacting the alkanol and the FCDA in a countercurrent mode, the alkanol is not only contacted with the FDCA intensely and during a relatively long period, but the vaporous alkanol also entrains water that is formed during the esterification. Therefore, the reaction vapor that leaves the reaction zone comprises mainly alkanol and water. The vapor stream is therefore relatively small and can be easily treated. Further, in the process of the present invention it is ascertained that the higher concentration of alkanol is in contact with the lower concentration of FDCA, which is beneficial for the yield of the esterification reaction. Moreover, in US2012/0220507 it is explicitly disclosed that the esterification of furandicarboxylic acid with an alcohol to give the corresponding esters always involves a temperature-dependent equilibrium developed between the reactants (acid and alcohol) and the products (ester and water), irrespective of the type of catalysis selected. In US2012/0220507 it is suggested to use an azeotrope former in order to shift the equilibrium in favor of the ester to help remove water from the reaction mixture. In the process according to the present invention water is continuously removed via the reaction vapor, whilst the esters of FDCA and FDCA itself remain in the liquid in the reaction zone. Thereby the equilibrium of the esterification is shifted, which also benefits the yield of the esterification reaction. No addition of another extraneous agent, such as an azeotrope former is needed. From the teachings in US 2012/0220507 it is apparent that the yield of the esterification reaction in the process configuration of WO 2013/191938 the maximum obtainable yield of the diester is the equilibrium. Now that in the process according to the present invention the equilibrium is shifted, this process obtains an increased yield vis-á-vis the process according to WO 2013/191938.

It is advantageous if the boiling point of the alkanol is not too high. The vaporization of alcohols with a low boiling point requires relatively little energy. The alcohol vapors will also entrain water formed during the esterification rather easily. Since the alkanols having 1 to 4 carbon atoms have atmospheric boiling points below 120° C., which is in the same order of magnitude as the boiling point of water, the alkanol preferably comprises 1 to 4 carbon atoms, and is preferably methanol. In this way the boiling points between the alkanols and water on the one hand and the boiling point of the mono- and diester of FDCA on the other hand are sufficiently different to facilitate the separation. Since methanol does not form an azeotrope with water, the separation of water and methanol is fairly simple and, thus, the use of methanol is especially advantageous.

As already indicated above, the countercurrent mode in which the process is being carried out represents a significant advantage over the process according to the prior art. Such countercurrent modes may be carried out in a variety of reactors. Suitable reactor types include tubular reactors, trickle-bed reactors, slurry bubble columns and monolith reactors. The reaction zone according to the present invention may be comprised in any of these reactors. Advantageously, the reaction zone according to the present invention comprises a reactive stripping column. In the stripping column the vaporous stream of the alkanol entrains any water formed and facilitates the removal of water thereby shifting the equilibrium of the esterification towards the ester products.

Suitably, the reactor is of the type that reduces backmixing. Therefore, the reactor advantageously comprises internals, preferably sieve plates and/or a packing. The internals or packings further promote contact between the vaporous phase and the liquid phase. The internals may be configured as conventional distillation trays, comprising down-comers, bubble caps and the like. However, such configuration is not needed. Simple sieve plates comprising holes in plate-form may suffice. The packing may comprise inert particles, such as SiC or glass particles. However, it may be advantageous to employ a catalytically active packing. Therefore, the packing may comprise a solid catalyst. Such solid catalysts are preferably selected from the group consisting of acidic zeolites, ion exchange resins and mixtures thereof. It is not necessary or even desirable that all of the packing consists of catalytically active particles. The particles may be suspended in the liquid starting material. It is preferred that in the top portion of the reaction zone, where the alkanol concentration in the vapor stream is lower and the concentration of the alkyl esters of FDCA is relatively high, the packing is inert and provides contact surface for improving the separation between the ester compounds on the one hand and the alkanol on the other hand.

Advantageously, the reaction according to the present invention is conducted in the absence of an additional catalyst. The esterification reaction is auto-catalyzed; the acid function of the FDCA already provides for catalytic activity. The absence of any further component in the reaction zone reduces the risk of contamination of the product, either the liquid phase or the reaction vapor.

An example of a reactive stripping reactor is described in U.S. Pat. No. 5,679,312. The stripping reactor comprises a reactor column with a plurality of porous trays. Catalyst particles may be provided on the trays. An entrainment catching structure is provided in the upper part of the reactor column. A vaporous stream is withdrawn at the top of the column, whereas a liquid flows down onto the subsequent trays via down-comers and is finally collected at the bottom part of the column from which it is discharged.

The skilled person will understand that the trays loaded with catalysts can be replaced by monoliths or any other type of packing. A study of reactive stripping in monolith reactors is described in e.g. Industrial & Engineering Chemical Research, 2007, vol. 46, nr 12, pages 4149-4157.

It has been indicated that the present invention provides a process for the preparation of dialkyl esters of FDCA, wherein the yield of the esterification reaction is improved compared to the known process of WO 2013/191938. The skilled person will appreciate that during the contact of the FDCA with the alkanol not only the dialkyl ester is obtained, but that also the monoalkyl ester of FDCA is formed. The present process is especially advantageous when the liquid starting material comprises 2,5-furandicarboxylic acid and the monoester thereof. In such a case also the monoester is at least partially converted to the desired diester in the reaction zone. Amounts of 10 to 90% wt of the monoester, based on the weight of the monoester and FDCA can suitably be used. The mixture of the monoester of FDCA and FDCA is included in the at least partially liquid starting material that is countercurrently contacted with the vaporous stream of the alkanol. It does not mean that all components of the starting material must be liquid. In view of the high melting temperature of FDCA itself, the starting material typically comprises a slurry of solid FDCA and liquid monoester of FDCA.

Compounds that are contained in the liquid starting material that comprises FDCA and the monoester thereof can easily be obtained from the process that has been described in the above-mentioned U.S. Pat. No. 8,519,167 and WO2011/043661. In these documents the preparation of FDCA and esters thereof has been described by means of the oxidation of 5-hydroxymethylfurfural and derivatives thereof with an oxygen-containing gas. The reaction is suitably conducted over a catalyst system that comprises cobalt and manganese, and suitably also comprises bromine. Accordingly, the starting material preferably comprises the oxidation product of a compound selected from 5-hydroxymethylfurfural, an ether thereof, an ester thereof and mixtures of any such compounds, with an oxygen containing gas. In particular, the starting material is the oxidation product of an ether of 5-hydroxymethylfurfural. The ether is preferably the methyl or ethyl ether, more in particular the methyl ether. The oxidation of these ethers results in a mixture of FDCA and the monomethyl or monoethyl ester, respectively. Such has been described in the above-mentioned U.S. Pat. No. 8,519,167.

The process according to the present invention, employing a liquid starting material comprising FDCA, gives the opportunity to obtain purified product. It has been found that it is difficult to separate FDCA and the monoester thereof from by-products of the oxidation by distillation or crystallization. One such by-product is 5-formyl-2-furancarboxylic acid. Since the process according to the present invention enables the skilled person to esterify virtually any acid into its ester and since the esters are more easily separable from each other than their corresponding acids, this process gives the skilled person a tool to obtain purified FDCA in the form of its dialkyl ester.

The reaction vapor that comprises alkanol and water is typically withdrawn from the reaction zone at the upper part thereof. Preferably, the reaction vapor has been treated such that the level of entrained droplets of other components, such as the mono- or diester of FDCA is substantially inhibited. This may be accomplished by passing the reaction vapor through an entrainment catching structure as suggested in for instance U.S. Pat. No. 5,679,312. The reaction vapor then comprises substantially only water and alkanol, and optionally, some volatile by-products. An example of a possible volatile by-product is the dialkyl ether that may be formed from two molecules of the alkanol. Such ether is typically removed from the reaction zone together with the alkanol and water. The reaction vapor comprising the alkanol and water is preferably separated into an alkanol fraction and a water fraction. Any volatile by-product that is formed in the reaction zone and that is removed together with the alkanol and water in the reaction vapor is advantageously separated from the reaction vapor and recovered as a separate fraction. The separation of the reaction vapor may be conducted by means of condensation or partial condensation. For instance when the alkanol is butanol, the condensation of the entire reaction vapor may result in a two-phase liquid, having a butanol phase and a water phase. When the reaction vapor comprises methanol, the condensation may be done at a temperature below the boiling point of water but above the boiling point of methanol, thereby obtaining a vaporous methanol fraction, separated from a liquid water fraction. However, since it cannot be excluded that the reaction vapor contains, possibly minor, amounts of by-products, the reaction vapor is preferably separated by means of distillation. The distillation enables the skilled person to design the equipment such that the purity of each desired fraction can be obtained. That will allow the skilled person to separate the reaction vapor in an alkanol fraction with a desired purity, a water fraction with the desired purity and, to the extent needed, one or more other fractions containing any by-products.

Since the process enables the obtaining of a pure alkanol fraction from the reaction the alkanol fraction can be returned to the reaction zone in order to be contacted with the liquid starting material and be subjected to esterification. Therefore, the alkanol fraction is preferably recycled to the reaction zone.

The liquid phase that is withdrawn from the reaction zone contains the dialkyl ester of FDCA. Although the ester formation tends to occur to a greater extent than in the processes according to the prior art, the esterification may result in a composition that may still comprise a minor amount of the monoester, whereas the vast majority consists of the desired diester of FDCA. The esters are miscible at the reaction conditions and the liquid phase thus does not contain solid material. In order to enhance the yield of the desired diester of FDCA, the liquid phase containing these ester compounds is suitably subjected to a separation step, and, preferably, at least a portion of the liquid phase is recycled to the reaction zone. In the separation step, the liquid phase may be split in two or more fractions, wherein each fraction has the same composition. One such fraction can then be recycled to the reaction zone. It is possible that the liquid phase comprises a minor amount of heavy by-products in the form of high-boiling contaminants. By high-boiling contaminants are understood compounds that have a higher boiling point than the relevant monoester of FDCA. In order to avoid a build-up of these contaminants, another part of the liquid phase may suitably be discharged as a bleed stream. A portion of the liquid phase is obtained as the desired dialkyl ester product. The portion of the liquid fraction that is advantageously recycled can be in the range of 10 to 90% wt of the liquid phase, suitably from 25 to 85% wt. The bleed stream may amount from 0 to 10% wt of the liquid phase.

Since the liquid phase consists mainly of the dialkyl ester of FDCA, it means that when a portion of the liquid phase is being recycled to the reaction zone a relatively large amount of the dialkyl ester is recycled to the reaction zone. Such a recycle appeared to be advantageous, since the dialkyl ester functions as a carrier liquid for the monoester and the FDCA in the at least partially liquid starting material. The dialkyl ester of FDCA typically has a lower melting point than FDCA or its monoalkyl ester. By recycling the dialkyl ester the melting point of the liquid starting material and hence the required energy input into the liquid starting material is further reduced.

The at least partially liquid starting material advantageously comprises a carrier liquid, which may be a diluent or solvent. In the embodiment described above, the carrier liquid typically comprises the dialkyl ester of FDCA. Other liquid materials may also be used. Suitably, these diluents or solvents have a higher boiling point than the alkanol and water. A suitable example is dimethyl sulphoxide (DMSO). However, since the presence of extraneous compounds is preferably avoided, the dialkyl ester of FDCA is suitably used as carrier solvent. The amount of FDCA and the monoester of FDCA in the at least partially liquid starting material is suitably in the range of 10 to 100% wt, preferably from 10 to 60% wt, based on the amount of FDCA, monoester of FDCA and carrier liquid.

When the liquid phase contains a non-negligible amount of mono-ester, it is advantageous that the liquid phase is separated into a first fraction enriched in the monoester of 2,5-furandicarboxylic acid and a second fraction rich in the diester of 2,5-furandicarboxylic acid. At least a portion of said first fraction is then preferably recycled to the reaction zone.

The first and second liquid fraction of the liquid phase can be obtained by a range of separation techniques. Suitably, the liquid phase is separated into the first and second fraction by means of cooling crystallization, evaporative crystallization, melt crystallization, evaporation or a combination thereof. This ensures that the skilled person, at his discretion, can design the separation to the desired purity. The separation technique may be adjusted such that the desired purity is obtained. At the same time the amount of the first and second fraction may be determined by the operating conditions of the separation techniques. Suitably, the first fraction, enriched in the mono-ester, represents from 10 to 90% wt, preferably 25 to 85% wt of the liquid phase and the second fraction is in the range of 90 to 10% wt, suitably from 75 to 25% wt.

If the first fraction contains heavy by-products in the form of high-boiling contaminants, a part of the first fraction, other than the portion that is being recycled, may suitably be discharged as bleed stream. By high-boiling contaminants are understood compounds that have a higher boiling point than the relevant monoester of FDCA. The bleed stream may consist of 0 to 10% wt of the first fraction.

Alternatively, the separation may be carried out such that more than two fractions are obtained. Hence, it is possible to implement a separation technique that yields a third, fourth etc. fraction, in addition to the first fraction enriched in monoester and second fraction, rich in diester. In such a separation, any high boiling contaminants may be separated as an additional separate fraction.

The reaction conditions in the reaction zone preferably include a reaction temperature in the range of 150 to 300° C., preferably from 160 to 260° C., and a pressure of 5 to 25 bar. The residence time is suitably in the range of 0.1 to 3 hours, preferably from 0.3 to 1.5 hrs.

Although the process according to the present invention may be carried out in a batch or semi-batch mode, it is preferred to conduct this process as a continuous process.

The dialkyl ester product obtained from the process according to the present invention may be used as such, e.g. in the preparation of a polyester such as a poly(alkylene 2,5-furandicarboxylate). It is also possible to convert the ester product, which may contain both mono- and diester of FDCA, into pure FDCA in its acid form. For that purpose the alkyl ester of FDCA is hydrolyzed to the alkanol and FDCA. Therefore the alkyl ester product is advantageously contacted with water for hydrolysis or saponification, to obtain a product composition, comprising FDCA.

By saponification is understood the reaction of an ester with a base whereby an alcohol and salt of the acid is formed. The process usually involves the reaction of an aqueous alkali metal base, such as NaOH or KOH, with an ester to form an alkali metal salt. The alkali metal base is usually present in at least a stoichiometric amount to allow for the formation of the salt. Acidification of the salt results in the production of FDCA as the acid.

Hydrolysis of esters is well known in the art. The reaction comprises contacting the ester in question with water. Suitably, the water has been acidified or rendered alkaline. Acids and bases tend to catalyse the hydrolysis of the ester. Therefore, the purified esterified product is suitably contacted with water in the presence of a hydrolysis catalyst. The catalyst can be selected from a wide range of acid or alkaline compounds. It is most convenient to apply inorganic acids, such as sulphuric acid, hydrochloric acid, nitric acid and the like. Also the use of Lewis acids, such as aluminium trichloride, may be used. Suitable alkaline catalysts include the alkali metal hydroxides, such as sodium or potassium hydroxide, but salts of weak organic acids may also be used. Salts of formic acid, acetic acid, propionic acid or butyric acid are suitable examples. The cation can be any metal ion, such as an alkali metal ion or alkaline earth metal ion. Other metal salts of such weak organic acids, such as the zinc salts, may also be used. It is advantageous if the salts are soluble in water. The skilled person will realize that the nature of the hydrolysis catalyst is not of critical importance.

Although the hydrolysis catalyst may increase the reaction rate of the hydrolysis it may have the drawback that by introducing the catalyst an extraneous compound is added that may contaminate the resulting acids. Therefore, the hydrolysis of the purified esterified composition, i.e. the contact of the purified esterified composition with water, is suitably carried out in the absence of a hydrolysis catalyst. It has appeared that the conversion of the esters in the purified esterified composition is running smoothly also without an additional hydrolysis catalyst. Once the hydrolysis starts and FDCA and the monoester of FDCA are formed, the acidic functions of these compounds autocatalyze the hydrolysis further. Since the risk of contamination is being avoided by carrying out the hydrolysis in the absence of an additional hydrolysis catalyst, such a process is preferred.

Hydrolysis conditions are well known in the art. It is conventional to heat the ester in water in the presence or absence of an acid or a base. A suitable temperature range may be from 100 to 200° C. Since in the present case it has been found that it is advantageous to conduct the hydrolysis at temperatures above 100° C., it is desirable to apply a pressure above 1 bar. Therefore, the purified esterified composition is preferably contacted with water at a temperature of 120 to 180° C. and a pressure of 5 to 30 bar.

Saponification conditions may be the same as those of the hydrolysis. However, the temperature may even be lower, e.g. as low as 60° C. The hydrolysis temperature ranges suitably from 60 to 200° C. The pressure may range from about 1 to 30 bar.

BRIEF DESCRIPTION OF THE DRAWINGS

The process will be further illustrated by means of the following figures.

DETAILED DESCRIPTION OF THE INVENTION

Figure 1:
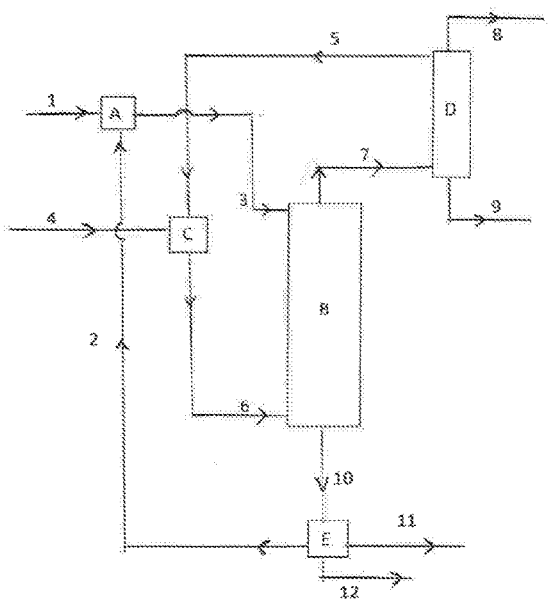
FIG. 1 shows a simplified flow scheme for the conversion of FDCA with an alkanol to the ester of FDCA.

Referring to FIG. 1, a stream comprising FDCA is supplied via a line 1 to a mixing zone A. The stream may be a slurry comprising solid FDCA and in addition the liquid monoester of FDCA, e.g. the monomethyl ester. In the mixing zone A the FDCA or mixture of FDCA and monoester thereof is combined with a liquid stream comprising the dialkyl ester of FDCA that is provided via a line 2. The liquid stream in the line 2 may also comprise a minor amount of monoalkyl ester of FDCA. The combined liquid stream is withdrawn from the mixing zone A via a line 3 and passed to a reaction zone B. Reaction zone B may be designed as a reactive stripping column. The combined liquid stream in the line 3 is then introduced into the upper part of the reactive stripping column B. The reactive stripping column B may be provided with sieve plates that contain holes to allow the flow of liquid from the top to the bottom, and the flow of vapor from the bottom to the top, whereas back-mixing is reduced. The vapor in the reactive stripping column B is provided by a stream of an alkanol that is introduced into the lower part of the stripping column B via a line 6. In the stripping column B esterification reactions between the FDCA and alkanol and between the monoester of FDCA and the alkanol take place while the alkanol is counter-currently contacted with the FDCA. Any water that is formed during the esterification is withdrawn as water vapor together with the alkanol vapor. Thereby the equilibrium of the esterification reaction is shifted and the esterification reaction is allowed to run to virtual completion. The reaction vapor comprising the alkanol and water is withdrawn from the top of the reactive stripping column and passed to a distillation column D through a line 7, to allow for the separation of the alkanol and water. During distillation in the distillation column D the water fraction is usually recovered as the bottom fraction and thus withdrawn from the bottom of the distillation column D via line 9. Water thus recovered is usually discharged.

It is possible that with the reaction vapor also some FDCA derivatives are entrained. This may in particular be the case for the dialkyl ester that tends to be the lower boiling derivative. If that is the case the dialkyl ester is suitably recovered from the stream of the line 7 in a separation zone.

This separation zone may be the same as or different from the distillation column D. If it is different, the separate separation zone may be positioned before or preferably after the distillation column D. In such a situation, the alkanol and any dialkyl ether are separated from the reaction vapor. The distillation residue, comprising the FDCA derivatives and water, is subsequently subjected to separation. This may be done by evaporation or another suitable separation technique, such as crystallization.

During the residence of the alkanol in the reactive stripping column B some by-products may have been formed, e.g. the dialkyl ether through the etherification of the alkanol in the acid environment of the column B. The dialkyl ether is then also separated from the alkanol and, when the ether is the fraction with the lower boiling point, will be withdrawn from the distillation column D via a line 8, whereas the alkanol is recovered and withdrawn from the distillation column D via a line 5.

The alkanol fraction in the line 5 is passed to a combination zone C, where it is combined with fresh make-up alkanol, provided via a line 4. The combined stream of alkanol is passed via the line 6 to the reactive stripping column B. In this way the alkanol is effectively recycled.

The dialkyl ester of FDCA that is formed in the reactive stripping column B is discharged as a liquid phase from the bottom part of the reactive stripping column B via a line 10. In the line 10 the liquid phase containing the dialkyl ester is passed to a splitting zone E. In the splitting zone E the liquid phase is split into a recycle stream that is passed via the line 2 to the mixing zone A, and into a product stream comprising the dialkyl ester of FDCA that is discharged via a line 11. As indicated above, the liquid phase may comprise a minor amount of heavy by-products in the form of high-boiling contaminants that may have been formed during the production of FDCA. In such a case it is effective to provide for a bleed stream. Such a bleed stream may be obtained by splitting the liquid phase of the line 10 in the splitting zone E into a further stream that is discharged via line 12.

As indicated in the description, the liquid phase may be subjected to a separation treatment in a separation zone in order to obtain a fraction that is even richer in dialkyl ester than the liquid phase. In such a case the splitting zone E is replaced by a separation zone, e.g. a crystallization or evaporation zone, to obtain a product stream rich in dialkyl ester and a recycle stream containing a major part of the monoalkyl ester that is contained in the liquid phase. If a bleed stream is considered, this may be derived directly from the separation zone. Alternatively, the bleed stream, if any, may be taken from the recycle stream that contains the monoalkyl ester, thereby avoiding the loss of dialkyl ester from the product stream.

The invention will be further illustrated by means of the following example.

Example

Figure 2:
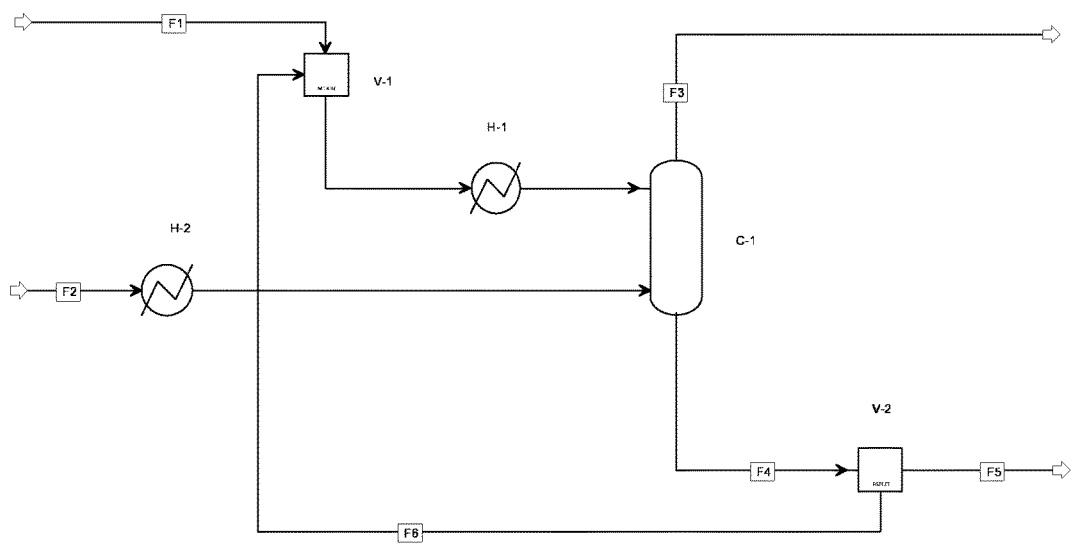
FIG. 2 shows an alternative further simplified process scheme which forms the basis for the experiment described below.

Reference is made to FIG. 2. A stream of a crude composition comprising a mixture of FDCA and the monomethyl ester thereof from an oxidation process (stream F1) is mixed in a feed tank (V-1) with a recycle stream F6 that is rich in the dimethyl ester of FDCA. The combined stream comprising solid FDCA is preheated by heat exchanger H-1 to 190° C., and then fed to the upper stage of a reactive stripping column C-1. This is a column operating at 5 bar with 15 plates, each of which has a residence time of 5 minutes.

A dry methanol stream F2 is heated and vaporized in a heater H-2 and fed below the lowest plate into the reactive stripping column C-1. As methanol goes up into the column, it partly dissolves in the liquid mixture where it reacts with FDCA and the monomethyl ester thereof to produce the dimethyl ester and water. The water formed vaporizes and leaves the column at the top together with non-reacted methanol and some entrained product (stream F3). As methanol is fed in excess to the column, the methanol vapor enhances the water vaporization. So the methanol is both reactant and stripping agent.

The bottom product of the stripping column C-1 (stream F4) is collected as the liquid phase in a crude ester tank V-2, from where 30% is withdrawn as product (stream F5) and the remainder is recycled to the feed tank V-1 (stream F6) to maintain a loop of the dimethyl ester of FDCA over the column.

The Table below shows the compositions and operating conditions of the main streams indicated above.

TABLE

| | Stream Number | | | | | |
|---|---|---|---|---|---|---|
| | F1 liquid starting material | F2 methanol stream | F3 reaction vapor | F4 liquid phase | F5 crude ester product | F6 recycle liquid phase |
| Temperature (° C.) | 20 | 20 | 211 | 175 | 175 | 175 |
| Pressure (bar) | 10 | 10 | 5 | 5 | 5 | 5 |
| Mass flow (kg/h) | | | | | | |
| Water | | | 1.3 | 0.0 | 0.0 | 0.0 |
| Methanol | | 10.0 | 7.4 | 0.9 | 0.3 | 0.6 |
| FDCA | 5.4 | | 0.0 | 0.0 | 0.0 | 0.0 |
| FDCA-monomethyl ester | 0.6 | | 0.1 | 0.1 | 0.0 | 0.1 |
| FDCA-dimethyl ester | | | 1.2 | 18.9 | 5.7 | 13.2 |

The invention claimed is:

1. A process for the preparation of dialkyl esters of 2,5-furandicarboxylic acid from a 2,5-furandicarboxylic acid-containing starting material, which process comprises:
contacting a vaporous stream of an alkanol countercurrently with the at least partially liquid starting material comprising the 2,5-furandicarboxylic acid in a reaction zone to conduct an esterification reaction to the dialkyl ester of 2,5-furandicarboxylic acid and water;
withdrawing a reaction vapor comprising the alkanol and water from the reaction zone, wherein water is removed via the reaction vapor, while the esters of 2,5-furandicarboxylic acid and the 2,5-furandicarboxylic acid remain in the liquid in the reaction zone; and
discharging a liquid phase comprising at least the dialkyl ester of 2,5-furandicarboxylic acid, from the bottom part of the reaction zone, to obtain the dialkyl ester of 2,5-furandicarboxylic acid.

2. The process according to claim 1, wherein the alkanol has 1 to 4 carbon atoms.

3. The process according to claim 1, wherein the reaction zone comprises a reactive stripping column.

4. The process according to claim 1, wherein the reaction zone comprises reactor internals and/or a packing.

5. The process according to claim 1, wherein the liquid starting material comprises 2,5-furandicarboxylic acid and the monoester thereof.

6. The process according to claim 1, wherein the starting material comprises the oxidation product of a compound selected from 5-hydroxymethylfurfural, an ether thereof, an ester thereof and mixtures of any such compounds, with an oxidizing agent.

7. The process according to claim 1, wherein the reaction vapor, comprising the alkanol and water, is separated into an alkanol fraction and a water fraction.

8. The process according to claim 7, wherein the reaction vapor is separated by means of distillation.

9. The process according to claim 7, wherein the alkanol fraction is recycled to the reaction zone.

10. The process according to claim 1, wherein a portion of the liquid phase is recycled to the reaction zone.

11. The process according to claim 10, wherein another part of the liquid phase is discharged as a bleed stream.

12. The process according to claim 1, wherein the liquid phase is separated into a first fraction enriched in the monoester of 2,5-furandicarboxylic acid and a second fraction rich in the diester of 2,5-furandicarboxylic acid.

13. The process according to claim 12, wherein at least a portion of the first fraction is recycled to the reaction zone.

14. The process according to claim 13, wherein another part of the first fraction is discharged as a bleed stream.

15. The process according to claim 12, wherein the liquid phase is separated into the first and second fraction by means of cooling crystallization, evaporative crystallization, melt crystallization, evaporation or a combination thereof.

16. The process according to claim 1, wherein the reaction conditions in the reaction zone include a reaction temperature in the range of 150 to 300° C., and a pressure of 5 to 25 bar.

17. The process according to claim 1, which process is conducted as a continuous process.

18. The process according to claim 2, wherein the alkanol is methanol.

19. The process according to claim 4, wherein the reaction zone comprises sieve plates.

20. The process according to claim 6, wherein the oxidizing agent is an oxygen-containing gas.

* * * * *